United States Patent [19]
Tustin et al.

[11] Patent Number: 6,121,498
[45] Date of Patent: Sep. 19, 2000

[54] METHOD FOR PRODUCING ACETALDEHYDE FROM ACETIC ACID

[75] Inventors: Gerald C. Tustin; Leslie S. Depew, both of Kingsport; Nick A. Collins, Fall Branch, all of Tenn.

[73] Assignee: Eastman Chemical Company, Kingsport, Tenn.

[21] Appl. No.: 09/069,953

[22] Filed: Apr. 30, 1998

[51] Int. Cl.$^7$ ............ C07C 47/00; C07C 45/00; B01J 23/00; B01J 23/42

[52] U.S. Cl. .......... 568/420; 568/401; 502/300; 502/326; 502/339

[58] Field of Search ............... 568/420, 401; 502/300, 325, 339

[56] References Cited

U.S. PATENT DOCUMENTS

| 4,237,073 | 12/1980 | Steppich et al. | 568/401 |
| 4,268,362 | 5/1981 | Ogawa et al. | 203/28 |
| 5,059,716 | 10/1991 | Joentgen et al. | 568/426 |
| 5,306,845 | 4/1994 | Yokohama et al. | 568/449 |
| 5,336,810 | 8/1994 | Van Geem et al. | 568/435 |

FOREIGN PATENT DOCUMENTS

| 0539274A1 | 4/1993 | European Pat. Off. . |
| 0700890A1 | 11/1996 | European Pat. Off. . |
| WO 96/18458 | 6/1996 | WIPO . |

OTHER PUBLICATIONS

J. Kondo et al., "Infrared Study of Hydrogenation of Benzoic Acid to Benzaldehyde on ZrO$_2$ Catalysts", *Bull. Chem. Soc., Jpn*, pp. 3085–3090, (1993).

R. Pestman et al., "Selective hydrogenation of acetic acid towards acetaldehyde", *Reel. Trav. Chim. Pays–Bas*, 113, pp. 426–430, (1994).

E.J. Grootendorst et al., "Selective Reduction of Acetic Acid to Acetaldehyde on Iron Oxides", *Journal of Catalysis*, 148, pp. 261–269, (1994).

R. Pestman et al., "The formation of ketones and aldehydes from carboxylic acids, structure–activity relationship for two competitive reactions", *Journal of Molecular Catalysis*, pp. 175–180, (1995).

Z.F. Pei et al., "On the intermediates of the acetic acid reactions on oxides: an IR Study", *Applied Surface Science*, 103, pp. 171–182, (1996).

(List continued on next page.)

*Primary Examiner*—Howard C. Lee
*Assistant Examiner*—Everett White
*Attorney, Agent, or Firm*—Harry J. Gwinell; Matthew W. Smith

[57] ABSTRACT

A method of producing acetaldehyde hydrogenates acetic acid in the presence of an iron oxide catalyst containing between 2.5 and 90 wt % Pd, more preferably 10 and 80 wt % Pd and most preferably 20 and 60 wt % Pd. The catalyst has a specific surface area of less than 150 m$^2$/g. Hydrogen and acetic acid are fed to a reactor in a hydrogen to acetic acid ratio of 2:1 to 25:1, more preferably in a hydrogen to acetic acid ratio of 3:1 to 15:1 and most preferably in a hydrogen to acetic acid ratio of 4:1 to 12:1. The hydrogenation is performed at a temperature of about 250° C. to 400° C., more preferably about 270° C. to 350° C. and most preferably about 280° C. to 325° C. The hydrogenation of acetic acid produces a partially gaseous product, and acetaldehyde is absorbed from the partially gaseous product with a solvent containing acetic acid. The gas remaining after the absorption step contains hydrogen, and this gas is recycled for the hydrogenation of acetic acid. The absorbed acetaldehyde is distilled to isolate same. After acetaldehyde is isolated from unreacted acetic acid and the other products via distillation, the unreacted acetic acid is separated from the other products using azeotropic distillation. Water is contained in the other products, and the azeotrope is an azeotrope of ethyl acetate and water. The unreacted acetic acid is separated in a column, and the column is controlled to contain an ethyl acetate rich azeotrope of ethyl acetate and water.

27 Claims, 2 Drawing Sheets

OTHER PUBLICATIONS

Pestman, et al., "Identification of the Active Sites in the Selective Hydorgenation of Acetic Acid to Acetaldehyde on Iron Oxide Catalysts", *Journal of Catalysis*, vol. 174, 1998, pp. 142–152.

Pestman, et al., "Reactions of Carboxylic Acids on Oxides", *Journal of Catalysis*, vol. 168, 1997, pp. 255–264.

Pavlova, et al., "Low–Temperature Co Oxidation on Iron Oxide Supported Palladium", *React.Kinet.Catal.Lett*, vol. 59, No. 1, 1996, pp. 103–110.

Abstract of Japanese Patent Publication No. 9–100254A, Apr. 15, 1997.

Chemical Abstracts, vol. 113, No. 8, Aug. 20, 1990, p. 136, Abstract No. 61684.

METHOD FOR PRODUCING ACETALDEHYDE FROM ACETIC ACID

BACKGROUND OF THE INVENTION

1. Field of the Invention

The present invention relates in general to producing acetaldehyde. More specifically, the present invention relates to producing acetaldehyde by hydrogenating acetic acid.

2. Description of the Related Art

Acetaldehyde is an important industrial chemical. It has been used as a starting material for the commercial manufacture of acetic acid, acetic anhydride, cellulose acetate, other acetate esters, vinyl acetate resins, synthetic pyridine derivatives, terephthalic acid, peracetic acid and pentaerythritol. Historically, acetaldehyde has been used to produce acetic acid, but improvements in technology have resulted in more economical acetic acid production from synthesis gas (a mixture of carbon monoxide and hydrogen). This development implies that it may be more economically attractive to produce acetaldehyde from acetic acid rather than to produce acetic acid from acetaldehyde if a technically viable route existed.

Acetaldehyde has been produced commercially by the reaction of ethanol with air at 480° C. in the presence of a silver catalyst. This process has been replaced by the current process, the Wacker oxidation of ethylene. Both of these processes start with ethylene, and the Wacker route is more direct and efficient than the ethanol oxidation route. Acetaldehyde has also been produced by the hydration of acetylene. This process uses mercury salts as a catalyst, and mercury handling can cause environmental and safety problems. The use of acetylene causes safety concerns, and the high cost of acetylene relative to ethylene has rendered this process obsolete. Acetaldehyde can also be produced by reacting synthesis gas over a rhodium on silica catalyst at elevated temperature and pressure, but the selectivity to acetaldehyde is poor, and the process has never been practiced commercially. Acetaldehyde has also been produced from the reaction of methanol with synthesis gas at elevated temperature and pressure using a cobalt iodide catalyst with a group 15 promoter, but this process also has never been practiced commercially. Although the Wacker process is the preferred commercial process at this time, it also has many undesirable aspects. These include the special safety and handling problems associated with reacting ethylene with oxygen and the very corrosive nature of the aqueous acidic chloride-containing reaction mixtures which necessitates very expensive materials of construction. Thus a need exists for an acetaldehyde synthesis that is an improvement over the existing known processes.

A potentially attractive means to synthesize acetaldehyde is by the hydrogenation of acetic acid. See reaction (I) below. However the carboxylic acid group is generally considered to be among the most difficult functional groups to reduce by catalytic hydrogenation. Aldehyde groups, conversely, are easily reduced by catalytic hydrogenation to alcohols. See reaction (II) below. Thus, under the conditions required to reduce a carboxylic acid, the aldehyde is often not isolated in good yield because the aldehyde is further reduced to an alcohol. Furthermore, when the carboxylic acid contains an α-hydrogen, conversion to a ketone, water and carbon dioxide can occur. See reaction (III) below. This reaction becomes more prevalent as the number of α-hydrogens increases. Thus, acetone can be readily formed from acetic acid at the temperatures typically used for reaction (I) (300–400° C.). The above discussed reactions related to hydrogen and acetic acid in the vapor phase are summarized below:

| | |
|---|---|
| (I) $CH_3CO_2H + H_2 \rightarrow CH_3CHO + H_2O$ | $\Delta G_{300° C.} = +0.8$ kcal/mole |
| | $\Delta G_{400° C.} = -0.04$ kcal/mole |
| (II) $CH_3CHO + H_2 \rightarrow CH_3CH_2OH$ | $\Delta G_{300° C.} = -0.4$ kcal/mole |
| | $\Delta G_{400° C.} = +2.5$ kcal/mole |
| (III) $2\ CH_3CO_2H \rightarrow CH_3COCH_3 + CO_2 + H_2O$. | |

The hydrogenation of acetic acid to acetaldehyde and water (reaction (I)) is a mildly endothermic reaction. So, the thermodynamics of this reaction improve as the temperature is increased. The subsequent reaction (II), the hydrogenation of acetaldehyde to ethanol, is exothermic, and this reaction becomes less favorable as the temperature increases. Since the equilibrium of the acetic acid hydrogenation is poor, the reaction must be run with an excess of hydrogen to achieve appreciable acetic acid conversion. Thus, on a thermodynamic basis, ethanol formation will be favored at temperatures of 300–400° C. Reaction (III), the formation of acetone, is essentially irreversible at all temperatures above 0° C. and becomes very favorable thermodynamically as the temperature is increased. Increasing the temperature significantly above 400° C. will not likely improve the selectivity to the desired acetaldehyde product because of increasing acetone production. Other reactions, such as the formation of methane, carbon oxides and C2 hydrocarbons also are relevant in acetic acid hydrogenation chemistry, but are of less importance than the three reactions described above unless excessively high temperatures are used. In some circumstances, the formation of ethyl acetate presumably through ethanol as an intermediate can also lower the selectivity to the desired acetaldehyde.

Thus, it appears that a major challenge in producing acetaldehyde via acetic acid hydrogenation is catalyst design. The ideal catalyst should facilitate the initial hydrogenation of acetic acid to acetaldehyde but have essentially no activity for the subsequent hydrogenation to ethanol nor for the dimerization reaction producing acetone. If a catalyst has even a small activity for conversion of acetaldehyde to ethanol or for the conversion of acetic acid into acetone, then extreme losses in acetaldehyde selectivity may occur if the reaction is operated beyond the equilibrium conversion level allowed for converting acetic acid and hydrogen into acetaldehyde and water. A need exists for a catalyst that selectively hydrogenates acetic acid to acetaldehyde.

Catalyst selectivity is only one requirement for a viable acetaldehyde synthesis. The synthesis must also be operated in a manner that will allow for the facile recovery of the very volatile acetaldehyde product, the recovery of byproducts and the recycle of unconverted reactants. Generally processes that hydrogenate carboxylic acids to aldehydes do so under conditions of about 1 bar pressure (all pressures given herein are in terms of absolute pressures) and hydrogen to carboxylic acid ratios approaching 50/1. Although these conditions may be sufficient for nonvolatile aldehydes, they are impractical for acetaldehyde which boils at 19–20° C. Thus, a need also exists for a process that converts acetic acid into acetaldehyde in a manner that is selective and provides for the economical recovery of the acetaldehyde.

In spite of the thermodynamic limitations surrounding the hydrogenation of carboxylic acids to aldehydes, several examples of this reaction appear in the prior art. Generally these reactions are performed at about 1 bar pressure in the vapor phase in a large excess of hydrogen at temperatures ranging between 200 and 500° C., and the reaction is most successful with aromatic carboxylic acids or aliphatic acids containing few α-hydrogens. Van Geem et al., in U.S. Pat. No. 5,336,810, describe a Mn/Zn/Al oxide catalyst that converts benzoic acid to benzaldehyde in the vapor phase at 330° C. in a large excess of hydrogen in 88.3% selectivity at 98.9% conversion. Joentgen et al., in U.S. Pat. No. 5,059,716, describe catalyst system based on titanium or vanadium oxides in conjunction with one or more metals selected from Cr, Mo, Co, Ni, Zn, Cd and Cu for the hydrogenation of aromatic and aliphatic carboxylic acids containing not more than one α-hydrogen at 325–425° C. at 1 bar in the presence of a large excess of hydrogen. Yokoyama et al., in *Stud. In Surf. Sci. and Cat.* 1994, 90, 47–58 and in *Bull Chem. Soc. Jpn.* 1993, 66, 3085–3090, describe the use of zirconium oxide and modified zirconium oxide catalysts for the hydrogenation of aromatic carboxylic acids to aldehydes under similar reaction conditions. Yokoyama et al., in U.S. Pat. No. 5,306,845, also describe the use of a purified chromium oxide catalyst for the hydrogenation of both aromatic and aliphatic carboxylic acids under similar reaction conditions. This patent gives several examples of the hydrogenation of high molecular weight acids, such as stearic acid. Acetic acid is also stated to be as a suitable acid, but no examples are given. Yokoyama et al. stress that the reason for the high purity requirement in the chromium oxide is to prevent the ketone formation reaction. Welguny et al., in European Patent Application EP 0 700 890 (1996), describe the use of oxide-supported tin catalysts for hydrogenation of a wide variety of carboxylic acids to aldehydes under the typical high-temperature, high-hydrogen, low-pressure conditions described previously. Although acetic acid is included in the claims of this patent application, the only examples are for aromatic carboxylic acids and for pivalic acid. Ferrero et al., in European Patent Application No. EP 539,274 (1993), describe Ru—Sn—B on alumina catalysts for hydrogenation of a wide variety of carboxylic acids to aldehydes under the typical high-temperature high-hydrogen low-pressure conditions described previously. Although the Ferrero patent application gives no examples for acetic acid hydrogenation, it is mentioned in the claims. Most of the Ferrero reference concerns the reduction of senecioic acid to prenal or the reduction of aromatic carboxylic acids to the corresponding aldehydes.

The most definitive work on the acetic acid hydrogenation to acetaldehyde is described by Ponec and coworkers in *Recl. Trav. Chim. Pays-Bas* 1994, 426–430, in *J. Catal.* 1994, 148, 261–269, in *J. Molecular Catalysis A: Chemical* 1995, 103, 175–180, in *Applied Surface Science* 1996, 103, 171–182, and in *J. Catal.* 1997, 168, 255–264. These workers have proposed a working mechanism for the reaction and have reported several examples of the conversion of acetic acid to acetaldehyde in good selectivity. The base catalysts for these reductions are partially reduced metal oxides having an intermediate metal-oxygen bond strength. Partially reduced iron oxide is the most selective metal oxide, and acetaldehyde selectivities almost as high as 80% could be obtained at 1.2 bar pressure and using a hydrogen/acetic acid ratio=50/1 at 321° C. Addition of 5 wt. % Pt to this catalyst further increases the selectivity to acetaldehyde to over 80%. With tin oxide, the addition of the Pt about doubles the selectivity, increasing it from about 40% to about 80%. Ponec mentions in *J. Catal.* 1997, 168, 255–264 that there is an optimum Pt level, and that increasing the Pt level above 1.25 atomic % actually decreases the selectivity.

Although the acetic acid hydrogenation process studied by Ponec and coworkers is very selective to acetaldehyde, it is impractical as a commercial way to produce acetaldehyde. The impracticality stems from the need to isolate and collect acetaldehyde (normal boiling point=19–20° C.) from a vapor stream where it is present in maximum concentrations of 2–3% (or less, depending on the conversion) at about 1 bar pressure. Water and byproducts must be removed from the mixture, and hydrogen and unconverted acetic acid must be recycled to the reactor. These operations require that the temperature be lowered considerably from the 300–400° C. reaction temperature. A practical process requires much lower hydrogen/acetic acid ratios and much higher reaction pressures than used by Ponec.

SUMMARY OF THE INVENTION

Accordingly, it is an object of the present invention to provide a method of producing acetaldehyde that avoids dangers associated with mercury and acetylene.

It is a further object of the present invention to provide a method of producing acetaldehyde that avoids handling problems associated with reacting ethylene and oxygen.

It is a still further object of the present invention to provide a method of producing acetaldehyde that avoids corrosive aqueous acidic acid chloride-containing reaction mixtures.

It is another object of the present invention to provide a method for hydrogenating acetic acid with good selectivity for producing acetaldehyde.

It is still another object of the present invention to provide a method for hydrogenating acetic acid that allows for easy recovery of volatile acetaldehyde.

These and other objects are accomplished by a method of producing acetaldehyde that hydrogenates acetic acid in the presence of an iron oxide catalyst containing between 2.5 and 90 wt % Pd, more preferably 10 and 80 wt % Pd and most preferably 20 and 60 wt % Pd. The catalyst has a specific surface area of less than 150 m$^2$/g. Hydrogen and acetic acid are fed to a reactor in a hydrogen to acetic acid ratio of 2:1 to 25:1, more preferably in a hydrogen to acetic acid ratio of 3:1 to 15:1 and most preferably in a hydrogen to acetic acid ratio of 4:1 to 12:1. The hydrogenation is performed at a temperature of about 250° C. to 400° C., more preferably about 270° C. to 350° C. and most preferably about 280° C. to 325° C. The hydrogenation of acetic acid produces a partially gaseous product, and acetaldehyde is absorbed from the partially gaseous product with a solvent containing acetic acid. The gas remaining after the absorption step contains hydrogen, and this gas is recycled for the hydrogenation of acetic acid. The absorbed acetaldehyde is distilled to isolate same. After acetaldehyde is isolated from unreacted acetic acid and the other products via distillation, the unreacted acetic acid is separated from the other products using azeotropic distillation. Water is contained in the other products, and the azeotrope is an azeotrope of ethyl acetate and water. The unreacted acetic acid is separated in a column, and the column is controlled to contain an ethyl acetate rich azeotrope of ethyl acetate and water.

BRIEF DESCRIPTION OF THE DRAWINGS

The invention will be readily understood by reference to the following description of the specific embodiments described by way of example only, with reference to the accompanying drawings, wherein.

DETAILED DESCRIPTION OF THE PREFERRED EMBODIMENTS

The present invention will now be described with preferred embodiments and examples which are given by way of example only, not limitation.

Figure 1:
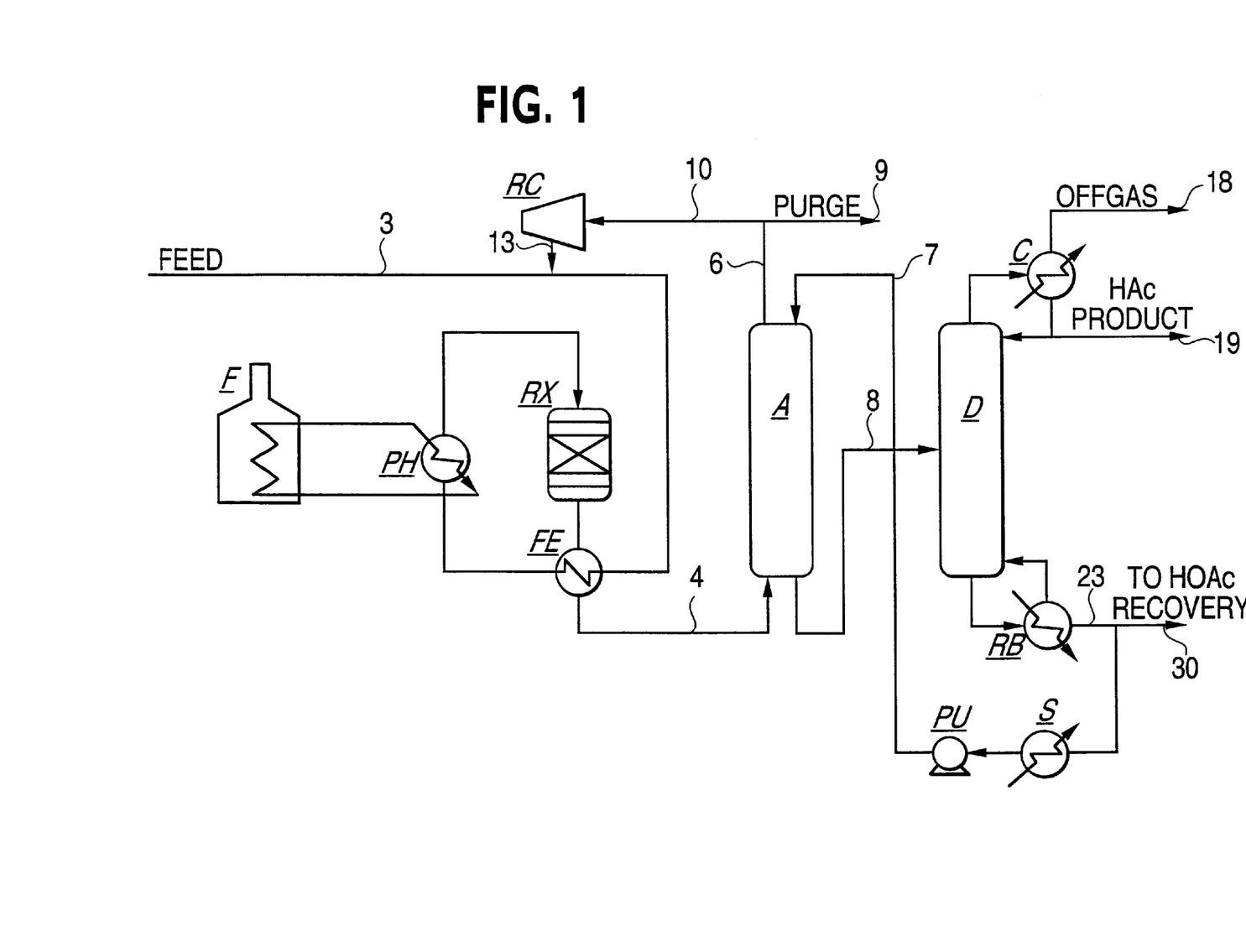
FIG. 1 is a schematic representation of components used to produce acetaldehyde.
Figure 2:
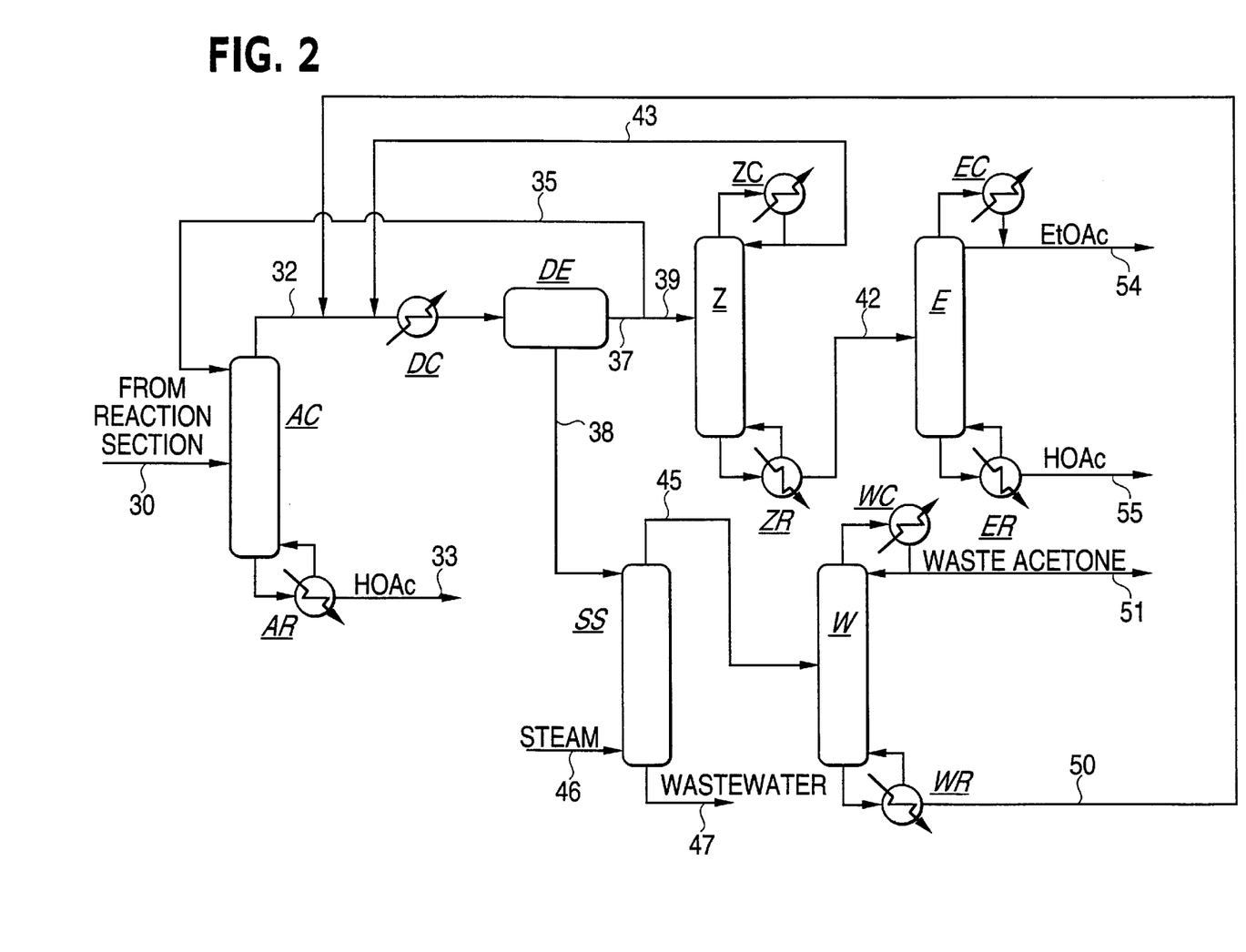
FIG. 2 is an schematic representation of components used to recover acetic acid.

A specific embodiment of the process of the invention consists of two main sections: a reaction section and a recovery section shown schematically in FIGS. 1 and 2, respectively. Acetic acid is converted to acetaldehyde and water with excess hydrogen in the reaction section over a catalyst containing iron and palladium in a fixed-bed reactor RX. The acetaldehyde product is recovered via distillation D after absorption A using the acetic acid-rich distillation bottoms as a solvent after cooling S.

Referring to FIG. 1, stream 3 is a feed to the reactor RX containing acetic and hydrogen. Although a 1-to-1 molar ratio is stoichiometrically sufficient for producing acetaldehyde, an excess of hydrogen is supplied in feed 3. The reactor RX contains an iron oxide/palladium catalyst. Before the feed is supplied to the reactor, it is heated with furnace F and reactor preheater PH. The product of reactor RX is fed to an absorber A. This product is hot and is cooled in feed effluent exchanger FE. Feed effluent exchanger FE also serves to preheat the feed 3 to the reactor. The product of reactor RX is substantially gaseous. Absorber A is used to liquify the acetaldehyde and other products. Cooled product 4 supplied to the absorber A and acetic acid feed 7 is also supplied. Acetic acid from feed 7 captures the products and allows hydrogen to pass via stream 6. A portion of the hydrogen is recycled via stream 10, recycle compressor RC and stream 13. Another portion of the hydrogen is purged via stream 9, and this maintains the purity of hydrogen. Recycle compressor RC compresses the hydrogen. Reactor RX and absorber A operate under pressure. The pressure in absorber A is from pressurized product in stream 4 and from pump PU.

The liquid coming off of absorber A as stream 8 is sent to distillation column D to recover acetaldehyde. The overhead from distillation column D is cooled via condenser C to condense same. A portion of the condensed liquid is sent back to the distillation column D as a reflux. Offgas 18 is not condensed and leaves the system shown in FIGS. 1 and 2. Acetaldehyde product comes from stream 19, and this also leaves apparatus shown in FIGS. 1 and 2. From the bottom of the distillation column, a re-boiler RB is provided to supply the more volatile compounds back to the distillation column D. Stream 23 is acetic acid rich and is partially recycled to the absorber A. As mentioned previously, the absorption in absorber A works best at lower temperatures, and solvent cooler S is provided for this purpose.

Stream 30 may contain ethyl acetate, water, acetic acid and acetone. To separate these compounds, the recovery apparatus shown schematically in FIG. 2 is employed. First, acetic acid column AC is used to separate out acetic acid. The boiling point of acetic acid is very close to that of water, and it would normally be difficult to separate these two components via distillation. To address this problem, ethyl acetate is fed to acetic acid column AC via stream 35. Ethyl acetate forms an azeotrope with water. The azeotrope has a boiling point significantly lower than either water or ethyl acetate. This enables separation. After acetic acid reboiler AR, acetic acid is recovered from stream 33. This acetic acid may be mixed with hydrogen and fed to reactor RX via stream 3.

The overhead from acetic acid column AC contains ethyl acetate, water and other products. Because water is difficult to separate from acetic acid as mentioned above, it is important that excess water not be supplied via stream 35. For this purpose, stream 32 is condensed in decanter cooler DC and then decanted in decanter DE. The aqueous phase leaves decanter DE in stream 38, and the organic phase leaves in stream 37. A portion of stream 37 is supplied back to the acetic acid column AC. Another portion of stream 37 is fed to azeotrope column Z via stream 39 to distill a "near" ethyl acetate-water azeotrope. The mixture is a "near" azeotrope because it does not contain the exact azeotropic ratio of ethyl acetate to water. As mentioned above, the azeotrope has a low boiling point and therefore can be removed as an overhead from azeotrope column Z. After azeo column condenser ZC, the azeotrope is indirectly recycled back to acetic acid column AC via stream 43.

From the bottom of azeotrope column Z, stream 42 is supplied to ethyl acetate column E after azeo column reboiler ZR. As mentioned above, excess hydrogenation of acetic acid produces ethanol. The ethanol can react with the acetic acid and produce ethyl acetate in an esterification process. This reaction occurs throughout the apparatus, whenever ethanol and acetic acid are present together. The reaction may be especially prominent when both reactants are in the liquid phase. Ethyl acetate column E separates ethyl acetate as an overhead. After ethyl acetate column condenser EC, stream 54 contains ethyl acetate which can be sold as a finished product. From the bottom of ethyl acetate column E, a somewhat small stream 55 of acetic acid is produced after ethyl acetate column reboiler ER.

As mentioned above, decanter DE separates aqueous products from organic products. The aqueous stream 38 is supplied to steam stripper SS. Steam stripper SS is a distillation column heated by steam 46. Lighter organics come off the top of steam stripper SS in stream 45 and waste water comes off the bottom as stream 47. The organics in stream 45 are supplied to waste acetone column W. Acetone has a very low boiling point, even lower than the azeotrope. Thus, a waste acetone stream 51 is produced after acetone column condenser WC. From the bottom of the waste acetone column W, a near ethyl acetate-water azeotrope stream 50 is recycled after acetone column reboiler WR.

The two azeotrope recycle streams 50 and 43 are not supplied directly back to the acetic acid column AC. Instead, they are fed to decanter cooler DC and decanter DE to remove water.

The processes depicted in FIGS. 1 and 2 are designed for optimum operation at the following conditions: 1) a 5/1 molar ratio of hydrogen to acetic acid in the reactor RX feed 3, 2) byproduct ethanol is converted to ethyl acetate as dictated by chemical equilibrium at of conditions present in the bottom of the acetaldehyde recovery column D, and 3) the reactor operates at 300° C., 17.2 bar, and 45% acetic acid conversion with a selectivity of 89% to acetaldehyde, 5% to ethanol, 4% to acetone (and $CO_2$), and 2% to methane and C2 hydrocarbons (ethylene plus ethane). If the degree of ethyl acetate formation from ethanol and unconverted acetic acid in the reactor RX is low, the reaction may be simply catalyzed by adding sulfuric acid to the HOAc-rich solvent before recovery. The recovery scheme shown in FIG. 2 is highly dependent on this conversion of byproduct ethanol to ethyl acetate and is a significant part of the present invention.

Mass-separating agents other than ethyl acetate are possible. Such agents may be selected from those organic compounds that from a minimum-boiling azeotrope with water and separate into water-rich and organic-rich liquid phases upon condensation. Those skilled in the art of separations may select such an alternate to ethyl acetate and modify the process depicted in FIG. 2 appropriately. However, as ethyl acetate is a coproduct of the process its use as an azeotroping agent avoids introducing another compound to the process and as such is used in the preferred embodiment.

In the preferred embodiment the azeotroping agent both forms a minimum boiling azeotrope with water and forms two liquid phases upon condensation. Potential azeotroping agents include, but are not limited to, acrylonitrile, allyl acetate, allyl acetone, allyl cyanide, benzene, 1-butanol, 1-butenylethyl ether, 1-butoxy-2-propanol, butyl acetate, butyl acetoacetate, butyl acrylate, n-butyl aniline, butyl benzoate, butyl butyrate, butyl chloride, butyl ether, butylisopropenyl ether, 2-butyl octanol, butyraldehyde, butyronitrile, carbon disulfide, carbon tetrachloride, 2-chloroethyl ether, chloroform, chloroisopropyl ether, crotonaldehyde, cyclohexane, cyclohexanone, cyclopentanone, diallyl acetal, diallyl amine, dibutyl acetal, dibutyl amine, dibutyl ethanolamine, 2,3-dichloropropanol, dicyclopentadiene, diethyl acetal, diethyl butyral, diisobutylene, diisobutyl ketone, dimethyl butyral, 2,5-dimethyl furan, 2,6-dimethyl-4-heptanol, dimethylisobutyral, dipropyl acetal, dipropyl ketone, epichlorohydrin, ethyl acetate, ethyl acrylate, n-ethyl aniline, ethylbenzene, 2-ethylbutanol, 2-ethylbutyl acetate, 2-ethylbutyl butyrate, ethylbutyl ether, ethylbutyl ketone, 2-ethylbutyraldehyde, ethylcrotonate, ethylene dichloride, ethyl formate, 2-ethylhexanol, 2-ethylhexyl acetate, 2-ethylhexyl amine, 2-ethylhexyl chloride, 2-ethylhexyl crotonate, 2-ethylhexyl ether, ethylidene acetone, 4-ethyloctanol, ethyl propionate, heptane, 2-heptyl acetate, 3-heptyl acetate, hexaldehyde, hexane, hexanol, 2-hexenal, hexyl acetate, hexyl chloride, isobutyl alcohol, isophorone, isopropyl acetate, isopropylbenzene, isopropyl chloride, isopropyl ether, mesityl oxide, methacrylaldehyde, 1-methoxy-1,3-butadiene, 3-methoxybutyl acetate, methylamyl ketone, methylene chloride, 2-methyl-5-ethyl pyridine, 5-methyl-2-hexanone, methylisobutyl ketone, methylisopropenyl ketone, n-methylmorpholine, 2-methyl pentanal, 2-methyl pentanol, 4-methyl-2-pentanol, 4-methyl-2-pentene, 4-methyl-2-pentyl acetate, 2-methylpropyl acetate, methylpropyl ketone, nonane, paraldehyde, pentane, 2,4-pentanedione, 3-pentanol, propionitrile, propyl chloride, propylene dichloride, styrene, tetrachloroethylene, 1,4-thioxane, toluene, triallyl amine, 1,1,2-trichloroethane, 1,1,2-trichloroethylene, valeraldehyde, valeric acid, vinyl acetate, vinylallyl ether, vinylbutyl ether, vinyl butyrate, vinyl crotonate, vinylethyl ether, vinyl-2-ethylhexyl ether, vinylisobutyl ether, vinyl isobutyrate, vinyl isopropyl ether, vinyl-2-methyl pentanoate, vinyl propionate, vinylpropyl ether, and m-xylene. Among these, ethyl acetate is preferred since, as mentioned above, it is a coproduct and its use does not introduce another component to the separation.

The catalyst (in reactor RX) of the invention contains iron and palladium. Catalysts can contain between about 2.5 and 90 wt % Pd with the balance of the weight calculated as $Fe_2O_3$ (the actual chemical nature of the iron may or may not be $Fe_2O_3$ depending on the specific method of catalyst synthesis used). More preferred catalysts contain between 10 and 80 wt % Pd based on $Fe_2O_3$. The most preferred catalysts contain between 20 and 60 wt % Pd based on $Fe_2O_3$. Catalysts containing low amounts of palladium perform well under low-pressure high-hydrogen conditions, but may not perform well under the high-pressure low-hydrogen conditions preferred in the invention. Catalysts containing low amounts of palladium may rapidly lose their activity and selectivity under the high-pressure low-hydrogen conditions preferred in the invention. Excessively high amounts of palladium are uneconomical and may produce excessive amounts of hydrocarbons. The active components of the catalyst of the invention can be supported, but the support should be unreactive for the conversion of acetic acid to acetone. The catalyst should have a surface area below 150 $m^2/g$. Catalysts with excessively high surface areas can exhibit reduced selectivity to the desired acetaldehyde. The catalysts of the invention may be reduced in hydrogen prior to their use in the reaction of hydrogen and acetic acid by contacting the catalysts with hydrogen at about between 50 and 500° C. and at about 1–50 bar pressure. More preferred prereduction conditions are between 200 and 400° C. and 1–20 bar pressure, and the most preferred prereduction conditions are between 250 and 350° C. and 1–5 bar pressure.

It is rather important that the catalyst be in a correct oxidation state, and the correct oxidation state should be readily regenerated under the reaction conditions. If the catalyst is in an over oxidized state, then acetone becomes the predominant product. The selective catalysts contain a mixture of zero valent metal and metal oxide phases. If the catalyst is in an over reduced state, methane becomes the predominant product. Addition of Pd to the catalyst facilitates the formation and maintenance of the desired oxidation state.

The catalysts of the invention are reactive and selective under a wide variety of conditions. Temperatures can range from about 250 to 400° C. More preferred temperatures range from 270 to 350° C., and the most preferred temperature range is from 280 to 325° C. At low temperatures the rate may be low and, if the mixture is low in hydrogen, the reaction can also be limited by the equilibrium restrictions dictated by the thermodynamics of the reaction. Excessively high temperature can lead to lower acetaldehyde selectivity due to the formation of acetone and hydrocarbons. Pressures can range from less than 1 bar to greater than 50 bars, and the catalysts will still have excellent rates and acetaldehyde selectivities provided the right temperatures and hydrogen to acetic acid ratios are used. At pressures of about 1 bar at 300° C. and at hydrogen to acetic acid ratio of about 40, excellent rates and conversion are seen even with $Fe_2O_3$ containing no Pd. The rate and selectivity under these conditions are even higher if Pd is added to the $Fe_2O_3$ in the levels preferred in the present invention. However the recovery and recycle portions of the process of the invention become impractical at these low-pressure high-hydrogen conditions. Lowering the hydrogen to acetic acid ratio at low pressure lowers the rate and conversion to impractical levels and places the catalyst in an unfavorable oxidation state causing increased selectivity to acetone. Generally an increase in hydrogen plus acetic acid pressure increases the rate and degree of acetic acid conversion if other conditions remain unchanged. Selectivity can also change as the pressure is increased. Ethyl acetate, which normally is not a significant product at low pressure, becomes a significant product as the pressure increases. Acetone, which can be a significant product under low-pressure low-hydrogen conditions, is not a significant product at high-pressure low-hydrogen conditions provided the catalyst contains about 20 wt % Pd based on $Fe_2O_3$. If the catalyst contains significantly less than about 20 wt % Pd based on $Fe_2O_3$, then the activity and acetaldehyde selectivity of the catalyst rapidly deteriorate with time on stream, and acetone and ethyl acetate selectivity increase under high-pressure low-hydrogen conditions. Pressures from acetic acid and hydrogen greater than 50 bars can cause increased selectivity to ethanol and ethyl acetate. However the use of diluents to increase the pressure significantly above 50 bars is within the spirit of the invention and can be done without harming the selectivity. In view of the above-mentioned considerations, the preferred pressure of acetic acid plus hydrogen for the process of the invention is between about 5 and 50 bars. A more preferred pressure of hydrogen plus acetic acid is between about 5 and 30 bars, and the most preferred pressure is between about 6 and 20 bars.

The catalysts of the invention are active under a wide range of hydrogen to acetic acid ratios. The rate of the reaction increases as the amount of hydrogen increases. The rate of reaction first increases as the amount of acetic acid increases then decreases as the amount of acetic acid increases further. As mentioned above excessive amounts of acetic acid at low pressure can place the catalyst in the wrong oxidation state giving low rates and increased selectivity to acetone. Acetaldehyde can be produced at hydrogen to acetic acid ratios ranging from about 2:1 to 50:1 or higher. However, in view of the recovery and recycle portions of the invention, the preferred hydrogen to acetic acid ratio ranges from about 2:1 to 25:1. More preferred hydrogen to acetic acid ratio ranges from about 3:1 to 15:1, and the most preferred ratio ranges from 4:1 to 12:1.

The gas hourly space velocity (GHSV, volumes of reactants contacting the catalyst per hour at reaction conditions) depends on the other parameters described previously. Generally the space velocity is chosen to provide the desired conversion. The selectivity to acetaldehyde decreases as the acetic acid conversion increases. This effect can be greater at very low hydrogen levels because once the equilibrium conversion level is reached any further reaction converts the acetaldehyde into ethanol and ethyl acetate. Under the most preferred conditions of temperature, hydrogen to acetic acid ratio and hydrogen plus acetic acid pressure it is preferred to keep the acetic acid conversion below 50% if acetaldehyde is the main product desired. If greater amounts of ethyl acetate are desired, then it is possible to operate the reaction so that the acetic acid conversion approaches 100%.

Separation of the reactor effluent into product and unconverted reactant streams requires a number of steps. In the preferred embodiment, the first step is the absorption in absorber A of acetaldehyde and compounds boiling higher than acetaldehyde (boiling point 19–20° C.) using a solvent rich in acetic acid. The conditions used in absorber A will be largely dictated by the temperature, pressure, and composition of the reactor effluent and the desired acetaldehyde recovery. Acetaldehyde recoveries over 50% are desired and may be obtained by proper choice of conditions. Generally, recovery improves with decreasing temperature, increasing pressure, and increasing solvent feed rate. This is why the temperature of the reactor effluent is decreased via a reactor feed-effluent heat exchanger FE as depicted in FIG. 1. Preferably, the temperature of the effluent will be reduced below 250° C. prior to absorption. More preferred are temperatures below 200° C. with temperatures below 150° C. most preferred.

The pressure in absorber A is important to acetaldehyde recovery and should be as high as practically possible. This pressure should be close to that used in the reactor after taking into account pressure drops and placement of the gaseous recycle compressor RC. As noted previously, catalyst selectivity to acetaldehyde suffers when the combined partial pressure of hydrogen and acetic acid exceeds 50 bars which effectively limits the absorber pressure to below 60 bar after accounting for diluents. So, a broad range of absorber pressure is 5 to 60 bar with pressures of 6 to 25 bars preferred.

The composition of the absorber solvent in stream 7 will depend on catalyst selectivity and acetic acid conversion in the reactor. It should contain mostly unconverted acetic acid, however, with at least 50 wt % acetic acid ranging up to 95 wt % at low conversion levels. Preferably the acetic acid content of stream 7 will be between 60 and 85 wt %. Solvent rates will be dictated by the desired acetaldehyde recovery in absorber A but should range between a solvent to absorber feed (stream 4) ratio of 0.1 to 20 wt/wt and preferably between 1 and 10 wt/wt.

The gaseous product of stream 6 from the absorber will contain mostly unconverted hydrogen and light gases formed as reaction byproducts. This stream will be largely recycled to the reactor with a purge rate set to maintain a desired hydrogen purity. While none of these light gases have been shown to have a deleterious effect on catalyst performance, it is expected that the hydrogen content of the gaseous recycle 13 should exceed 50 mol % with purities between 60 and 95 mol % preferred.

The second major separation step is recovery of the acetaldehyde via distillation in distillation column D. Column pressure is important for producing liquid stream 19 from this relatively low-boiling acetaldehyde component (19–20° C.) and should be as high as possible to minimize refrigeration requirements in the overhead condenser. Minimum column pressure is 1 bar with preferred pressures from 5 to 20 bar.

EXAMPLES

The examples that follow are intended to illustrate the process of the invention and are not intended to limit the scope of the invention.

General Experimental Methods

Acetic acid hydrogenations at one bar pressure were performed using a reactor system equipped with on-line gas chromatography. Metered gas flows were provided by six Tylan Model FC-260 mass flow controllers. Electric temperature control and monitoring were provided by a Dow Camile® control system interfaced with a Gateway Model 2000 486DX/33 computer. All gas delivery lines were teed into pressure relief columns containing water to prevent accidental over pressurization. Acetic acid was fed by metering hydrogen or nitrogen through a temperature-controlled vaporizer containing the acetic acid. The temperature of the vaporizer was maintained by a circulating water/ethylene glycol bath. Product analysis was performed by on-line gas chromatography utilizing a Hewlett-Packard Model 3790A gas chromatograph fitted with a 6 ft.×⅛ inch stainless steel column containing 80/120 Carbopack B/6.6% Carbowax® 20M. Products were analyzed by this on-line gas chromatograph with the column programmed for 80° C. for 0 minutes, 4° C./minute to 150° C. and 150° C. for 0 minute using a flame ionization detector. A 4-port Valco Industries sampling valve was used to send the feed mixture to the reactor or to the gas chromatograph for analysis. Two six-port Valco Industries gas chromatographic sampling valves containing 1 mL volume sample loops were used to sample the reactant stream or the product stream. All tubing lines connecting the exit of the acetic acid vaporizer, bypass valve, reactor, six-port sampling valves and the gas chromatograph were constructed of ⅛-inch stainless steel and were heated with temperature-controlled heating tapes to 150° C. The three sampling valves were heated to 150° using valve ovens. The reactor was constructed of main section of 8-inch long×8 mm O.D. borosilicate glass fused to a lower section consisting of 6-inch long×7.5 mm O.D.–3 mm I.D. capillary tubing. The reactor had a 1-inch long×8 mm O.D. borosilicate side arm situated at 90° and 1 inch down from the top of the 8 mm O.D. glass portion of the main reactor section. The three openings to the reactor were fitted with 2-inch long ¼-inch O.D. kovar metal tubing sealed to the end of the glass. Accurately weighed catalyst charges (typically 0.2 g) were loaded into the reactor by first inserting a glass or quartz wool plug from the top of the reactor into the top part of the capillary section and then placing the catalyst charge on top of the glass or quartz wool plug. A thermocouple was inserted through the top of the reactor into the catalyst bed and sealed to the kovar tube with Swagelok® fittings. The reactant mixture was fed through the side arm, and the product exited at the base of the reactor. The kovar portions of the reactor inlet and outlet were connected to the stainless steel transfer lines using Swagelok® fittings. The reactor was heated with a vertically-mounted single element electric furnace containing a 12-inch long heat zone. The apparatus allowed for additional hydrogen or inert gas to be metered into the vapor stream exiting the temperature-controlled vaporizer. The acetic acid partial pressure could be controlled by altering the temperature of the vaporizer or by adding hydrogen or inert gas to the vapor stream exiting the temperature-controlled vaporizer. The apparatus could also easily be configured to allow inert gas to be metered to the temperature-controlled vaporizer. This flexibility in setting the feed composition facilitated the study of the reaction kinetics. Normally catalysts were reduced in hydrogen (22.4 standard cubic centimeters per minute, SCCM) overnight at 300° C. before feeding the acetic acid and hydrogen mixture.

In some cases a higher temperature was used for the reduction. When the reactor was idle between acetic acid hydrogenation experiments with the same catalyst charge, hydrogen flow (22.4 SCCM) was maintained at 300° C.

High pressure acetic acid hydrogenation reactions were performed in a reactor constructed from a 12 inch length of Hastelloy C tubing having an outer diameter of ¼ inch. All gas flow, pressure and temperature control devices were controlled by a Camile® Model 3300 process monitoring and control system interfaced with an IBM Model 750-P90 computer. Hydrogen flow was provided by a Brooks mass flow controller, and acetic acid was fed using dual ISCO high pressure syringe pumps. The device was fitted with a relief valve set for 35 bar. Pressure was controlled by a modified Research Control Valve with a pressure transducer located between the flow controller and the reactor. A 2-micron filter was placed between the reactor and the Research Control Valve. The product exiting the Research Control Valve was fed to a Valco Industries 6-port gas chromatographic sampling valve containing a 1 mL sample loop. The gas chromatographic sampling valve was interfaced to a Hewlett-Packard Model 3790A gas chromatograph fitted with a 6 ft.×⅛ inch stainless steel column containing 80/120 Carbopack B/6.6% Carbowax® 20M. Products were analyzed by this on-line gas chromatograph with the column programmed for 80° C. for 0 minutes, 4° C./minute to 150° C. and 150° C. for 0 minute using a flame ionization detector. The transfer lines, filter and Research Control Valve connecting the reactor to the gas chromatographic sampling valve were heated to 200° C. by a temperature-controlled heating tape. The gas chromatographic sampling valve and the transfer line connecting it to the gas chromatograph were maintained at 150° C. The reactor tube was loaded to position the accurately weighed catalyst charge (typically 0.2 g) in the middle of the reactor. Quartz fines (1 inch layer), 12×20 mesh quartz chips (3.5 inches layer) and quartz or glass wool plugs were placed on both sides of the catalyst charge. The entire length of the reactor was heated with a temperature-controlled heating tape. The acetic acid was delivered to the reactor via a line passing concentrically through the reactor head and about an inch into the upper portion of the heated portion of the reactor. The hydrogen delivery line and the relief valve were also fitted to the reactor head. Thus the upper portion of the heated reactor acted as an acetic acid vaporization and vapor mixing zone. Catalysts were reduced in hydrogen (25 SCCM) at 1.7 bar at 300° C. in the reactor over night or longer before feeding hydrogen and acetic acid. Reactions were started by setting the hydrogen and acetic acid feeds to the desired rates at the 1.7 bar setting and then setting the pressure to the desired amount. When the reactor was idle between acetic acid hydrogenation experiments with the same catalyst charge, hydrogen flow (22.4 SCCM) at 1.7 bar was maintained at 300° C.

The following definitions apply to the specific examples:
Space velocity (SV or GHSV)=volumes of gas per volume of catalyst per hour under reaction conditions,
Space time yield (STY)=grams of product produced per liter of catalyst per hour,
% acetic acid conversion=100(mmoles acetic acid reacted)/(mmoles acetic acid fed), % acetic acid accountability=100(mmoles acetic acid recovered+mmoles acetate equivalents in products)/ (mmoles acetic acid fed), % normalized selectivity=100(mmoles product)/(total mmoles all products).

Catalysts

The catalysts used in the examples were obtained by the methods that follow.

Catalyst No. 1: $Fe_2O_3$. $Fe_2O3$ (Aldrich, lot #DQ15808DQ, 99.98% purity) was used as received.

Catalyst No. 2: 2.5% Pd on $Fe_2O_3$. A solution was prepared from $Pd(NO_3)_2xH_2O$ (442 mg, Alfa lot #120982, 39.9% Pd) and water (10 mL). This solution was added to 20×40 mesh Catalyst No. 1 (7.1607 g) contained in an evaporating dish. The mixture was dried on the steam bath and calcined in a muffle furnace for 4 hours at 400° C.

Catalyst No. 3: 5% Pd on $Fe_2O_3$. A solution was prepared from $Pd(NO_3)_2xH_2O$ (127 mg, Alfa lot #120982, 39.9% Pd) and water (2 mL). This solution was added to Catalyst No. 1 (1.0294 g) contained in an evaporating dish. The mixture was dried on the steam bath and calcined in a muffle furnace for 5 hours at 400° C.

Catalyst No. 4: 10% Pd on $Fe_2O_3$. A solution was prepared from $Pd(NO_3)_2xH_2O$ (251 mg, Alfa lot #120982, 39.9% Pd), $Fe(NO_3)_3.9H_2O$ (5.06 g, Mallinckrodt lot #5032 KHTJ) and water (10 mL). To this solution was added a separate solution prepared from citric acid (2.59 g, Eastman Chemical Company plant material) and water (5 mL). The mixture was evaporated on the steam bath to a scaly mass and then calcined in a muffle furnace for 5 hours at 400° C.

Catalyst No. 5: 20% Pd on $Fe_2O_3$. A solution was prepared from $Pd(NO_3)_2xH_2O$ (501 mg, Alfa lot #120982, 39.9% Pd), $Fe(NO_3)_3.9H_2O$ (5.06 g, Mallinckrodt lot #5032 KHTJ) and water (10 mL). To this solution was added a separate solution prepared from citric acid (2.23 g, Eastman Chemical Company plant material) and water (5 mL). The mixture was evaporated on the steam bath to a scaly mass and then calcined in a muffle furnace for 5 hours at 400° C.

Catalyst No. 6: 40% Pd on $Fe_2O_3$. A solution was prepared from $Pd(NO_3)_2xH_2O$ (Alpha lot #120982, 39.9% Pd), $Fe(NO_3)_3x9H_2O$ (Mallinckrodt lot #5032 KHTJ) and water (10 mL). To this solution was added a separate solution prepared from citric acid (Eastman Chemical Company plant material) and water (5 mL). The mixture was evaporated on the steam bath to a scaly mass and then calcined in a muffle furnace for 5 hours at 400° C. The amount of $Pd(NO_3)_2xH_2O$ used in Catalyst No. 5 was approximately doubled to achieve 40% Pd.

Catalyst No. 7: 80% Pd on $Fe_2O_3$. A solution was prepared from $Pd(NO_3)_2xH_2O$ (2.005 g, Alfa lot #120982, 39.9% Pd), $Fe(NO_3)_3.9H_2O$ (1.01 g, Mallinckrodt lot #5032 KHTJ) and water (10 mL). To this solution was added a separate solution prepared from citric acid (1.93 g, Eastman Chemical Company plant material) and water (5 mL). The mixture was evaporated on the steam bath to a scaly mass and then calcined in a muffle furnace for 5 hours at 400° C.

Catalyst No. 8: Pd sponge. Pd sponge (20 mesh, Alfa lot #00777) was used as received.

Example 1

This example illustrates the effect of changing the weight percentage of Pd on $Fe_2O_3$ by large amounts under a standard set of feed conditions at one bar pressure. The example illustrates that acetic acid conversion is low when the catalyst contains 0 or 100% Pd and that the selectivity to methane is high. The example also illustrates that, of those catalysts converting over 90% of the acetic acid, the catalyst containing 10 wt % Pd produces acetaldehyde at the highest rate and selectivity with the lowest methane selectivity. The example further shows that although the catalyst containing no Pd had the highest acetaldehyde selectivity, it also had the lowest acetic acid conversion. The relationship between acetaldehyde selectivity and conversion will become more apparent in subsequent examples. The data for Example 1 were collected at a point in time when the catalyst activity was high and are presented in Table 1.

Example 2

This example compares the performance of catalysts containing 2.5 and 5 wt % Pd under conditions of comparable acetic acid conversion. The same feed conditions used in Example 2 were used as in Example 1, and the data were collected after the catalyst activity had moderated thus allowing for the lower conversions. The example illustrates that the catalyst containing 5 wt % Pd is more selective than that containing 2.5 wt % Pd when run at the same level of acetic acid conversion. The example further illustrates that much higher acetaldehyde selectivity at much higher acetic acid conversion can be achieved with catalysts containing Pd than the $Fe_2O_3$ catalyst of Example 1. The data for Example 2 are presented in Table 2.

Example 3

This example compares the performance of catalysts containing 5 and 10 wt % Pd under conditions of comparable acetic acid conversion. The same feed conditions used in Example 3 were used as in Example 1, and the data were collected while the catalyst activity was highest thus allowing for the higher conversions. The example illustrates that the catalyst containing 10 wt % Pd is more selective than that containing 5 wt % Pd when run at the same level of acetic acid conversion. The example further illustrates that, at one bar pressure, the optimum performance is achieved when the Pd level of 10 wt %. The data for Example 3 are presented in Table 3.

Example 4

This example illustrates the effects of changing the mole fraction of acetic acid in hydrogen ($X_{HOAc}$) at various space velocities on the performance of the 5 wt % Pd on $Fe_2O_3$ at one bar pressure. The example illustrates that high acetaldehyde selectivity can be achieved at high acetic acid mole fraction, but that it is difficult to obtain higher conversions by lowering the space velocity when the acetic acid mole fraction is high at one bar pressure. The data for Example 4 are presented in Table 4.

Example 5

This example illustrates the performance of the 10 wt. % Pd on $Fe_2O_3$ at 250 psig pressure and at a 5/1 hydrogen/ acetic acid ratio as a function of time on stream. The example illustrates that good rate and acetaldehyde selectivity can be achieved, but that the rate, conversion and acetaldehyde selectivity decrease after a certain time on stream. The example also illustrates that the selectivity to hydrocarbons is very low under the high-pressure low-hydrogen conditions. The example further illustrates that ethyl acetate is a significant product under the high-pressure low-hydrogen conditions. The performance data for Example 5 are presented in Table 5.

Example 6

This example illustrates the performance of the 40 wt % Pd on $Fe_2O_3$ at 17.2 bar gauge pressure at 7/1 and 5/1 hydrogen/acetic acid ratios with time on stream. This example also illustrates that the performance of this catalyst does not deteriorate in the manner exhibited by the 10 wt % Pd catalyst of Example 5. The performance data for Example 6 are presented in Table 6.

TABLE 1

Effect of 0 to 100 wt % Pd on the Performance of $Fe_2O_3$ Catalysts

| Wt % Pd | 0 | 10 | 20 | 40 | 80 | 100 |
|---|---|---|---|---|---|---|
| Catalyst No. | 1 | 4 | 5 | 6 | 7 | 8 |
| % HOAc Conv. | 19 | 96 | 98 | 99 | 81 | 26 |
| G/(1-hr) HAc | 280 | 499 | 157 | 79 | 45 | 1 |
| % HAc sel.* | 80 | 56 | 38 | 35 | 15 | 4 |
| % acetone sel. | 0.6 | 3.1 | 2.7 | 1.1 | 0.2 | 0.3 |
| % EtOH sel. | 7 | 38 | 50 | 55 | 22 | 0.4 |
| % $CH_4$ sel. | 10.5 | 2.7 | 8.5 | 8.6 | 62.9 | 95.4 |
| % $C_2$ H. C. sel.** | 3.1 | 0.1 | 0.7 | 0.3 | 0 | 0.1 |
| % HOAc acct.*** | 100 | 100 | 108 | 107 | 105 | 100 |

Conditions: 90 SCCM $H_2$ containing 2 mol % HOAc, 0.2 g catalyst, 300° C.
*Selectivities are normalized.
**$C_2$ Hydrocarbons = ethylene + ethane.
***Acetic acid accountability.

TABLE 2

Effect of % Pd on the Performance of $Fe_2O_3$ Catalysts

| Wt % Pd | 2.5 | | | | 5 | | | | |
|---|---|---|---|---|---|---|---|---|---|
| % HOAc Conv. | 54 | 50 | 52 | 50 | 45 | 59 | 51 | 48 | 45 |
| G/(1-hr) HAc | 597 | 621 | 656 | 698 | 527 | 748 | 694 | 674 | 662 |
| % HAc sel.* | 78 | 79 | 77 | 80 | 73 | 82 | 84 | 84 | 84 |
| % acetone sel. | 0.8 | 0.8 | 0.9 | 0.8 | 1.6 | 0.7 | 0.7 | 0.6 | 0.6 |
| % EtOH sel. | 15 | 15 | 17 | 14 | 18 | 12 | 10 | 9 | 9 |
| % $CH_4$ sel. | 4.6 | 4.1 | 4.4 | 3.8 | 6.1 | 5.2 | 5.7 | 5.9 | 5.9 |
| % $C_2$ H. C. sel.** | 1.0 | 0.9 | 0.9 | 0.8 | 1.6 | 0.7 | 0.7 | 0.6 | 0.6 |
| % HOAc acct.*** | 91 | 107 | 103 | 103 | 101 | 97 | 101 | 102 | 105 |

Conditions: 90 SCCM H2 containing 2 mol % HOAc, 0.2 g catalyst, 300° C.
*Selectivities are normalized.
**$C_2$ Hydrocarbons = ethylene + ethane.
***Acetic acid accountability.

Example 7

This example illustrates the integrated process of the invention. The processing steps of the invention are depicted in FIGS. 1 and 2. The reactor (a) is loaded with a Pd/$Fe_2O_3$ catalyst of the invention and operated at 300° C. with a 5/1 molar hydrogen to acetic acid ratio at 17.2 bar pressure, and the reaction is 89% selective to acetaldehyde, 5% selective to ethanol /ethyl acetate, 4% selective to acetone and CO2, and 2% selective to hydrocarbons at 45% acetic acid conversion. Ethanol is converted to ethyl acetate as dictated by the chemical equilibrium conditions in the bottom of the acetaldehyde recovery column (I). Optional sulfuric acid catalyst can be used to facilitate the attainment of the ethanol-acetic acid-water-ethyl acetate equilibrium. The heat and material balances for the process of the invention operating in this mode are provided in Tables 7 and 8.

While the invention has been described in connection with the preferred embodiments and examples, it will be understood that modifications within the principle outlined above will be evident to those skilled in the art. Thus, the invention is not limited to the preferred embodiments and examples, but is intended to encompass such modifications.

TABLE 3

Effect of % Pd on the Performance of $Fe_2O_3$ Catalysts: Comparison at the 5 and 10 Wt. % Levels

| Wt % Pd | 5 | | 10 | |
|---|---|---|---|---|
| % HOAc Conv. | 98 | 92 | 97 | 91 |
| G/(1-hr) HAc | 642 | 779 | 773 | 994 |
| % HAc sel.* | 36 | 47 | 52 | 68 |
| % acetone sel. | 1.1 | 0.9 | 1.0 | 1.0 |
| % EtOH sel. | 44 | 39 | 40 | 27 |
| % $CH_4$ sel. | 14 | 11 | 5.4 | 3.4 |
| % $C_2$ H.C. sel.** | 3.7 | 2.6 | 1.0 | 0.6 |
| % HOAc acct.*** | 98 | 103 | 98 | 103 |

Conditions: 90 SCCM H2 containing 2 mol % HOAc, 0.2 g catalyst, 300° C.
*Selectivities are normalized.
**$C_2$ Hydrocarbons = ethylene + ethane.
***Acetic acid accountability.

TABLE 4

Effect of Changing the Mole Fraction of Acetic Acid in Hydrogen
on the Performance of 5 wt. % Pd/Fe2O3
at Different Space Velocities.

| TTOS, min.* | 5350 | 7033 | 7141 | 8134 | 8886 | 9291 | 9328 | 9396 |
|---|---|---|---|---|---|---|---|---|
| SCCM H2 | 90 | 30 | 90 | 90 | 90 | 90 | 25 | 25 |
| GHSV, hr$^{-1}$ | 73000 | 24000 | 73000 | 73000 | 73000 | 73000 | 20000 | 20000 |
| $X_{HOAc}$ | 0.057 | 0.095 | 0.095 | 0.026 | 0.20 | 0.20 | 0.20 | 0.20 |
| % HOAc conv. | 38 | 31 | 16 | 66 | 23 | 16 | 17 | 26 |
| G/(1-hr) HAc | 1003 | 283 | 497 | 740 | 523 | 899 | 338 | 407 |
| % HAc sel.** | 87 | 87 | 89 | 79 | 87 | 90 | 89 | 89 |
| % Acetone sel. | 1.1 | 1.1 | 0.9 | 0.9 | 2.5 | 1.8 | 3.9 | 3.0 |
| % EtOH sel. | 8.0 | 6.8 | 5.3 | 15.8 | 7.5 | 5.8 | 4.6 | 5.4 |
| % CH$_4$ sel. | 3.2 | 4.8 | 3.9 | 3.7 | 2.7 | 1.8 | 1.9 | 2.2 |
| % C$_2$ H. C. sel.*** | 0.6 | 0.8 | 0.5 | 0.7 | 0.2 | 0.4 | 0.3 | 0.6 |
| % HOAc acct.**** | 86 | 82 | 91 | 92 | 81 | 95 | 96 | 89 |

Conditions: 0.2 g catalyst, 300° C.
*TTOS = total time on stream under hydrogen and acetic acid feed.
**Selectivities are normalized.
***C$_2$ Hydrocarbons = ethylene + ethane.
****Acetic acid accountability.

TABLE 5

Effect of Time on Stream on the Perfomance of 10 wt % Pd/Fe$_2$O$_3$
at 250 psig and 5/1 Hydrogen/Acetic Acid Ratio.

| TTOS, min* | 1739 | 2089 |
|---|---|---|
| % HOAc Conv. | 22 | 10 |
| G/(1-hr) HAc | 3350 | 970 |
| % HAc sel.** | 77.9 | 62.7 |
| % acetone sel. | 1.5 | 4.6 |
| % EtOH sel. | 15.0 | 16.2 |
| % EtOAc sel. | 4.6 | 15.5 |
| % CH$_4$ sel. | 0.7 | 0.7 |
| % C$_2$ H.C. sel.*** | 0.2 | 0.1 |

Conditions: GHSV = 12200, 300° C.
*TTOS = total time on stream under hydrogen and acetic acid feed.
**Selectivities are normalized.
***C$_2$ Hydrocarbons = ethylene + ethane.

TABLE 6

Effects of Hydrogen/Acetic Acid Ratio and Time on Stream on the
Performance of 40 wt % Pd/Fe$_2$O$_3$ at 250 psig.

| TTOS, min* | 512 | 534 | 2318 |
|---|---|---|---|
| H$_2$/HOAc | 7 | 5 | 5 |
| GHSV, hr-1 | 3530 | 2600 | 2600 |
| % HOAc Conv. | 46 | 42 | 38 |
| G/(1-hr) HAc | 1530 | 2125 | 2175 |
| % HAc sel.** | 86.4 | 77.1 | 77.0 |
| % acetone sel. | 1.7 | 1.3 | 1.5 |
| % EtOH sel. | 9.6 | 15.9 | 15.2 |
| % EtOAc sel. | 2.1 | 5.6 | 6.3 |
| % CH$_4$ sel. | 0.1 | <0.1 | <0.1 |
| % C$_2$H C. sel.*** | 0 | <0.1 | <0.1 |

Conditions: 300° C.
*TTOS = total time on stream under hydrogen and acetic acid feed.
**Selectivities are normalized.
***C$_2$ Hydrocarbons = ethylene + ethane.

TABLE 7

HOAc Hydrogenation Reaction Section Balance

| Stream | 11 | 13 | 18 | 19 | 23 | 30 | 31 | 33 | 36 |
|---|---|---|---|---|---|---|---|---|---|
| Temperature C | 67.3 | 77.6 | 37.8 | 37.8 | 167.8 | 167.8 | 167.8 | 37.8 | 66.7 |
| Pressure BAR | 19.0 | 19.0 | 6.9 | 6.9 | 6.6 | 6.6 | 6.6 | 2.8 | 19.0 |
| Vapor Fraction | 0.848 | 1.000 | 1.000 | 0.000 | 0.010 | 0.010 | 0.010 | 0.000 | 0.847 |
| Mole Flow KGMOL/HR | 4982 | 3845 | 22 | 318 | 4466 | 737 | 3729 | 3729 | 4982 |
| Mass Flow KG/HR | 63088 | 18807 | 510 | 13455 | 183638 | 30312 | 153325 | 153325 | 63086 |
| Volume Flow M3/HR | 6348 | 5914 | 84 | 18 | 465 | 77 | 389 | 155 | 6333 |
| Enthalpy MJ/HR | −388810 | −57092 | −2148 | −61647 | −1624722 | −268188 | −1356535 | −1397118 | −388610 |
| Mole Flow KGMOL/HR | | | | | | | | | |
| HOAC | 742.54 | 15.63 | 0.00 | 0.00 | 2265.66 | 373.98 | 1891.67 | 1891.67 | 748.43 |
| H2 | 3742.14 | 3332.30 | 5.28 | 0.05 | 0.00 | 0.00 | 0.00 | 0.00 | 3742.14 |
| HAC | 33.21 | 33.21 | 5.94 | 293.39 | 0.30 | 0.05 | 0.25 | 0.25 | 33.21 |
| METHANE | 358.78 | 356.76 | 8.40 | 2.95 | 0.00 | 0.00 | 0.00 | 0.00 | 358.76 |
| ACETONE | 2.59 | 2.59 | 0.00 | 0.06 | 26.65 | 4.40 | 22.25 | 22.25 | 2.59 |
| ETHANOL | 0.23 | 0.23 | 0.00 | 0.00 | 6.11 | 1.01 | 5.10 | 5.10 | 6.12 |

TABLE 7-continued

HOAc Hydrogenation Reaction Section Balance

| Stream | 11 | 13 | 18 | 19 | 23 | 30 | 31 | 33 | 36 |
|---|---|---|---|---|---|---|---|---|---|
| ETHENE | 28.43 | 28.43 | 1.28 | 2.18 | 0.00 | 0.00 | 0.00 | 0.00 | 28.43 |
| H2O | 28.98 | 28.98 | 0.11 | 16.85 | 2071.76 | 341.98 | 1729.78 | 1729.78 | 23.09 |
| CO2 | 39.37 | 39.37 | 1.49 | 2.61 | 0.00 | 0.00 | 0.00 | 0.00 | 39.37 |
| ETOAC | 5.89 | 5.89 | 0.00 | 0.00 | 95.49 | 15.76 | 79.73 | 79.73 | 0.00 |
| Mass Fraction | | | | | | | | | |
| HOAC | 0.7070 | 0.0500 | 0.0000 | 0.0000 | 0.7410 | 0.7410 | 0.7410 | 0.7410 | 0.7120 |
| H2 | 0.1200 | 0.3610 | 0.0210 | 0.0000 | 0.0000 | 0.0000 | 0.0000 | 0.0000 | 0.1200 |
| HAC | 0.0230 | 0.0790 | 0.5130 | 0.9610 | 0.0001 | 0.0001 | 0.0001 | 0.0001 | 0.0230 |
| METHANE | 0.0910 | 0.3090 | 0.2840 | 0.0040 | 0.0000 | 0.0000 | 0.0000 | 0.0000 | 0.0910 |
| ACETONE | 0.0020 | 0.0080 | 0.0000 | 0.0003 | 0.0080 | 0.0080 | 0.0080 | 0.0080 | 0.0020 |
| ETHANOL | 0.0002 | 0.0008 | 0.0000 | 0.0000 | 0.0020 | 0.0020 | 0.0020 | 0.0020 | 0.0040 |
| ETHENE | 0.0130 | 0.0430 | 0.0700 | 0.0050 | 0.0000 | 0.0000 | 0.0000 | 0.0000 | 0.0130 |
| H2O | 0.0080 | 0.0280 | 0.0040 | 0.0230 | 0.2030 | 0.2030 | 0.2030 | 0.2030 | 0.0070 |
| CO2 | 0.0270 | 0.0930 | 0.1280 | 0.0090 | 0.0000 | 0.0000 | 0.0000 | 0.0000 | 0.0270 |
| ETOAC | 0.0080 | 0.0280 | 0.0000 | 0.0000 | 0.0460 | 0.0460 | 0.0460 | 0.0460 | 0.0000 |

TABLE 8

HOAc Hydrogenation Recovery Section Balance

| Stream | 1 | 2 | 3 | 5 | 7 | 8 | 9 | 12 |
|---|---|---|---|---|---|---|---|---|
| Temperature C | 167.8 | 96.8 | 141.5 | 43.3 | 43.3 | 43.3 | 43.3 | 102.2 |
| Pressure BAR | 8.8 | 2.1 | 2.1 | 2.1 | 2.1 | 2.1 | 2.1 | 2.1 |
| Vapor Fraction | 0.006 | 1.000 | 0.000 | 0.000 | 0.000 | 0.000 | 0.000 | 0.000 |
| Mole Flow KGMOL/HR | 737.5 | 1490.7 | 382.8 | 1136.1 | 1198.6 | 353.3 | 62.6 | 16.9 |
| Mass Flow KG/HR | 30323 | 87620 | 22466 | 79762 | 84156 | 7270 | 4394 | 1445 |
| Volume Flow M3/HR | 61.4 | 22170.6 | 24.8 | 89.5 | 94.4 | 7.6 | 4.9 | 1.8 |
| Enthalpy MJ/HR | −268378 | −515645 | −169455 | −473168 | −499232 | −102244 | −26065 | −7813 |
| Mole Flow KGMOL/HR | | | | | | | | |
| HOAC | 374.10 | 28.74 | 370.36 | 25.00 | 26.38 | 2.41 | 1.38 | 1.36 |
| ACETONE | 4.40 | 87.36 | 0.00 | 82.96 | 87.53 | 4.96 | 4.57 | 0.09 |
| ETHANOL | 1.01 | 10.92 | 0.00 | 9.91 | 10.46 | 1.60 | 0.55 | 0.01 |
| H2O | 342.15 | 587.71 | 12.47 | 238.03 | 251.14 | 336.28 | 13.11 | 0.01 |
| ETOAC | 15.77 | 795.05 | 0.00 | 779.28 | 822.21 | 7.98 | 42.93 | 15.41 |
| HAC | 0.05 | 0.92 | 0.00 | 0.87 | 0.92 | 0.05 | 0.05 | 0.00 |
| Mass Fraction | | | | | | | | |
| HOAC | 0.7410 | 0.0200 | 0.9900 | 0.0190 | 0.0190 | 0.0200 | 0.0190 | 0.0570 |
| ACETONE | 0.0080 | 0.0580 | 0.0000 | 0.0600 | 0.0600 | 0.0400 | 0.0600 | 0.0040 |
| ETHANOL | 0.0020 | 0.0060 | 0.0000 | 0.0060 | 0.0060 | 0.0100 | 0.0060 | 0.0004 |
| H2O | 0.2030 | 0.1170 | 0.0100 | 0.0540 | 0.0540 | 0.8330 | 0.0540 | 0.0001 |
| ETOAC | 0.0460 | 0.7990 | 0.0000 | 0.8610 | 0.8610 | 0.0970 | 0.8610 | 0.9390 |
| HAC | 0.0001 | 0.0005 | 0.0000 | 0.0005 | 0.0005 | 0.0003 | 0.0005 | 0.0000 |

What is claimed is:

1. A method of producing acetaldehyde, comprising the steps of:
   (a) hydrogenating acetic acid at a pressure between about 5 and 50 bars in the presence of an iron oxide catalyst containing between 20 and 90 wt % palladium to produce a gaseous product; and
   (b) absorbing acetaldehyde from the gaseous product with a solvent containing acetic acid.

2. The method according to claim 1, wherein the catalyst contains between 20 and 80 wt % palladium.

3. The method according to claim 1, wherein the catalyst contains between 20 and 60 wt % palladium.

4. The method according to claim 1, further comprising the step of supplying hydrogen and acetic acid to a reactor in a hydrogen to acetic acid ratio of 2:1 to 25:1.

5. The method according to claim 1, further comprising the step of supplying hydrogen and acetic acid to a reactor in a hydrogen to acetic acid ratio of 3:1 to 15:1.

6. The method according to claim 1, further comprising the step of supplying hydrogen and acetic acid to a reactor in a hydrogen to acetic acid ratio of 4:1 to 12:1.

7. The method according to claim 1, wherein the iron oxide is $Fe_2O_3$.

8. The method according to claim 1, wherein the hydrogenation is performed at a temperature of about 250° C. to 400° C.

9. The method according to claim 1, wherein the hydrogenation is performed at a temperature of about 270° C. to 350° C.

10. The method according to claim 1, wherein the hydrogenation is performed at a temperature of about 280° C. to 325° C.

11. The method according to claim 1, wherein the catalyst has a specific surface area of less than 150 $m^2/g$.

12. The method according to claim 1, wherein the step of absorbing acetaldehyde is run at a temperature below 250° C.

13. The method according to claim 1, wherein the step of absorbing acetaldehyde is run at a temperature below 200° C.

14. The method according to claim 1, wherein the step of absorbing acetaldehyde is run at a temperature below 150° C.

15. The method according to claim 1, wherein step (b) produces a gaseous remainder containing hydrogen, the gaseous remainder being recycled to step (a) for the hydrogenation of acetic acid.

16. The method according to claim 1, further comprising the step of (c) distilling the absorbed acetaldehyde from the solvent containing acetic acid.

17. The method according to claim 16, wherein step (c) is performed at a pressure of 1 bar or greater.

18. The method according to claim 16, wherein step (c) is performed at a pressure from 5 to 20 bar.

19. The method according to claim 16, wherein step (c) produces acetaldehyde product and a mixture of ethyl acetate, water, acetic acid and acetone, the method further comprising the step of (d) recovering the acetic acid from the mixture of ethyl acetate, water, acetic acid and acetone using an azeotropic distillation.

20. The method according to claim 19, wherein a heterogeneous water azeotrope is used for the azeotropic distillation.

21. The method according to claim 19, wherein an azeotrope of ethyl acetate and water is used for the azeotropic distillation.

22. The method according to claim 21, wherein the unreacted acetic acid is separated in a column, and the column is controlled to contain an ethyl acetate rich azeotrope of ethyl acetate and water.

23. The method according to claim 19, wherein step (a) is conducted in a reactor zone, the method further comprising the step of returning acetic acid recovered in step (d) to the reactor zone.

24. The method according to claim 19, further comprising the step of (e) recovering ethyl acetate, water and acetone from the mixture of ethyl acetate, water, acetic acid and acetone using decantation, steam stripping and distillation.

25. The method according to claim 16, wherein step (c) produces acetaldehyde product and a mixture containing acetic acid, a portion of the mixture containing acetic acid being used in step (b) as the solvent for absorbing acetaldehyde.

26. A process for the preparation and recovery of acetaldehyde comprising the steps of:
   (a) contacting within a reactor zone hydrogen and acetic acid with a hydrogen to acetic acid molar ratio of less than 25 in the presence of an iron oxide catalyst containing between 20 and 90 wt. % palladium at temperatures between 250 and 400° C. and pressures between 5 and 50 bar;
   (b) absorbing the reaction product in acetic acid-rich solvent and returning a major portion of the uncondensed gases to the reactor zone;
   (c) distilling the acetaldehyde from the acetic acid-rich solvent;
   (d) recovering unconverted acetic acid by azeotropic distillation;
   (e) returning the recovered acetic acid to the reactor zone; and
   (f) recovering the coproducts water, acetone and ethyl acetate by decantation, steam stripping and distillation.

27. A method of producing acetaldehyde, comprising the steps of:
   (a) supplying hydrogen and acetic acid to a reactor in a hydrogen to acetic acid ratio of 2:1 to 25:1; and
   (b) hydrogenating acetic acid in the reactor at a pressure between about 5 and 50 bars and a temperature of about 250° C. to 400° C., the hydrogenation being conducted in the presence of an iron oxide catalyst containing between 20 and 60 wt. % palladium.

* * * * *